US009962393B1

(12) United States Patent
Summers

(10) Patent No.: US 9,962,393 B1
(45) Date of Patent: May 8, 2018

(54) METHOD FOR TREATING VASCULAR DISEASE BY ADMINISTERING A LIPOSOMAL PROSTAGLANDIN COMPOSITION

(71) Applicant: ANGIOSOMA RESEARCH, INC., Montgomery, TX (US)

(72) Inventor: David P Summers, Montgomery, TX (US)

( * ) Notice: Subject to any disclaimer, the term of this patent is extended or adjusted under 35 U.S.C. 154(b) by 22 days.

(21) Appl. No.: 15/187,079

(22) Filed: Jun. 20, 2016

Related U.S. Application Data

(60) Provisional application No. 62/182,610, filed on Jun. 21, 2015, provisional application No. 62/182,613, filed on Jun. 21, 2015.

(51) Int. Cl.
*A61K 9/127* (2006.01)
*A61K 31/5575* (2006.01)
*A61K 9/00* (2006.01)

(52) U.S. Cl.
CPC ........ *A61K 31/5575* (2013.01); *A61K 9/0019* (2013.01); *A61K 9/127* (2013.01)

(58) Field of Classification Search
CPC .................................................... A61K 9/127
See application file for complete search history.

(56) References Cited

U.S. PATENT DOCUMENTS

| 4,103,026 | A | * | 7/1978 | Carlson | A61K 31/19 514/530 |
| 4,935,237 | A | * | 6/1990 | Higgins | C12Y 304/21069 424/94.63 |
| 5,082,664 | A | * | 1/1992 | Lenk | A61K 9/127 264/4.3 |
| 5,718,917 | A | * | 2/1998 | See | A61K 9/0034 424/450 |
| 5,925,375 | A | * | 7/1999 | Lenk | A61K 9/127 424/450 |

OTHER PUBLICATIONS

Carlson, L.A. and Olsson, AG. (1979) "PGE1 in Ischaemic Peripheral Vascular Disease." In Karim, S.M.M. (Ed.), Practical Applications of Prostaglandins and Their Synthesis Inhibitors (pp. 39-51). Lancaster, England: MTP Press Limited.*
ClinicalTrials.gov (2004). "Prostaglandin E1 (Liprostin) Treatment With Lower Limb Angioplasty for Peripheral Arterial Occlusive Disease."*

* cited by examiner

*Primary Examiner* — Benjamin Packard
(74) *Attorney, Agent, or Firm* — Nick A Nichols, Jr.

(57) ABSTRACT

In a multilamellar liposome, a pharmaceutical agent is encapsulated in the liposome in the absence of a partition enhancing buffer. Preferably, the pharmaceutical agent is prostaglandin E1 (PGE1). The pharmaceutical agent may be administered to a mammal in an amount effective to treat vascular disease. The release of the pharmaceutical agent from the multilamellar liposome may be regulated by proper selection of liposome size, dosage of the pharmaceutical agent, lipid to pharmaceutical agent weight ratio, and rate of infusion of the pharmaceutical agent.

15 Claims, 3 Drawing Sheets

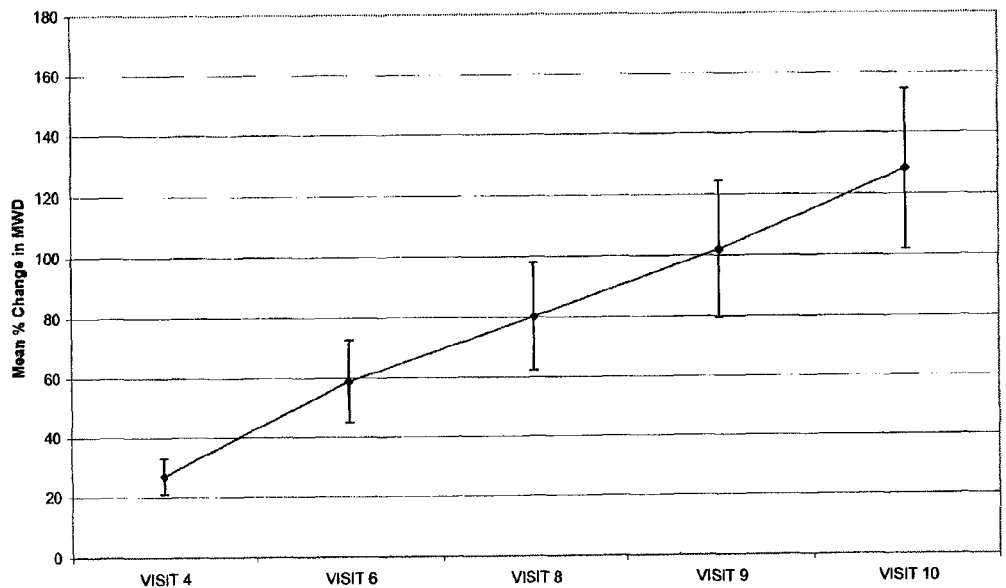
Figure 1. Percentage Change in Maximum Walking Distance from Baseline by Visit
Intent-to-Treat Population (N = 80)
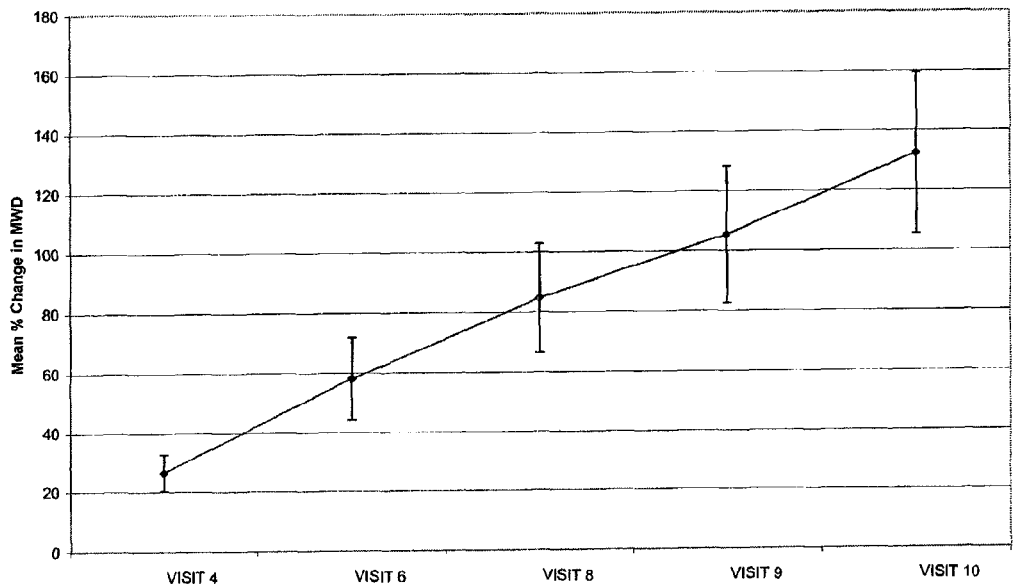
Figure 2. Percentage Change in Maximum Walking Distance from Baseline by Visit
Efficacy Population (N=75)

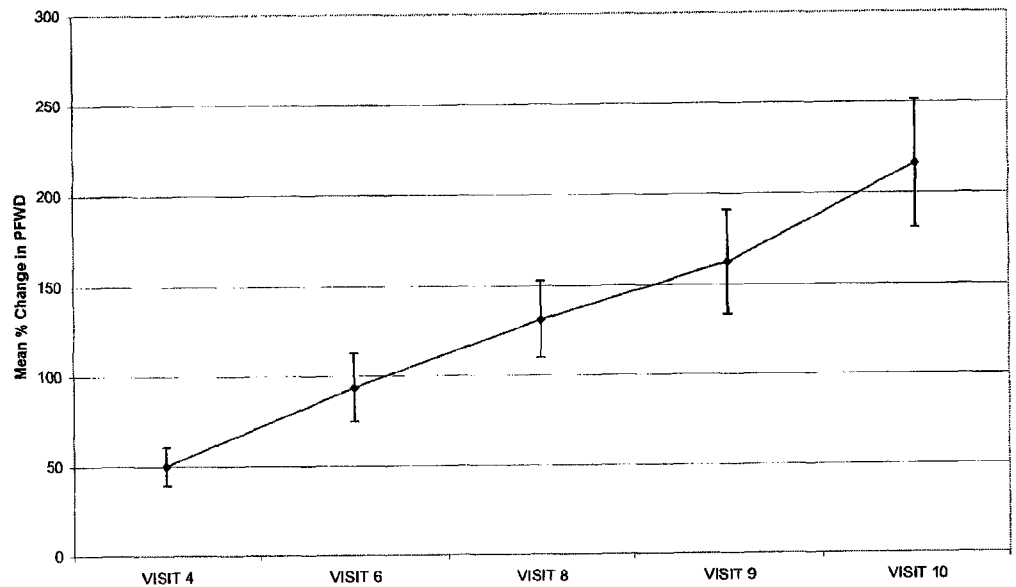
Figure 3. Percentage Change in Pain-Free Walking Distance from Baseline by Visit
Intent to Treat Population (N=80)
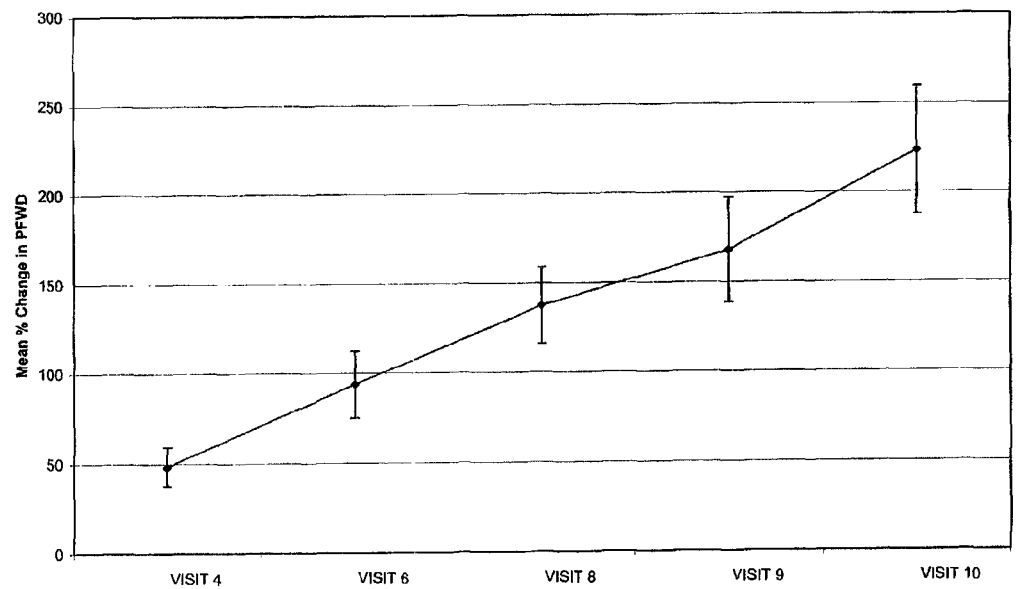
Figure 4. Percentage Change in Pain-Free Walking Distance from Baseline by Visit
Efficacy Population (N=75)

METHOD FOR TREATING VASCULAR DISEASE BY ADMINISTERING A LIPOSOMAL PROSTAGLANDIN COMPOSITION

CROSS-REFERENCE TO RELATED APPLICATION

This application claims the benefit of U.S. Provisional Application Ser. No. 62/182,610, filed Jun. 21, 2015, and U.S. Provisional Application Ser. No. 62/182,613, filed Jun. 21, 2015, which applications are incorporated herein by reference.

BACKGROUND

The present invention relates in general to treatments for vascular disease, and more particularly to a method for treating vascular disease by administering a liposomal prostaglandin formulation to a mammal.

Prostaglandins are cyclic, oxygenated fatty acids known to be potent pharmacological agents and to have a potent effect on cell function in many organ systems. Prostaglandin E1 (PGE1), for example, has various pharmacological properties, the most notable being vasodilation, inhibition of platelet aggregation, and stimulation of intestinal and uterine smooth muscle. Major disadvantages of PGE1, however, are its short in-vivo half-life of approximately 30 to 90 seconds, instability, and rapid degradation. When administered intravenously, PGE1 is rapidly metabolized during circulation through the lungs so that its pharmacological effects are significantly diminished by the time it reaches a target site or organ system.

Encapsulation of PGE1 in liposomes solves the problems of instability, short term half-line and rapid degradation experienced with PGE1 in its free form. Liposomes may function as sustained release systems for drugs, and the rate of release may be manipulated. A liposomal formulation of pharmaceutical agents results in a more effective targeted delivery, enabling delivery of the maximum patient tolerated dosage with fewer side effects.

U.S. Pat. No. 4,103,026 describes a method of treating peripheral vascular disease by non-arterial administration of PGE1. The patent discloses that PGE1 in a saline solution is administered intravenously at a dose of 1-10 µg/hr for 10 to 20 minutes once per hour. Even though the PGE1 passes through the patient's lungs before transportation to the patient's extremities, therapeutic effects are reported. Administration of PGE1, however, is limited to hourly injections over an extended period of time. In Example 1 of the patent, the PGE1 dosage disclosed is 2-4 µg/hr administered intravenously for 10 minutes each hour for 3 days.

U.S. Pat. No. 5,925,375 describes the use of multilamellar liposomal prostaglandin formulations for treatment of disorders characterized by cellular activation and adhesion, inflammation and/or toxemia. The liposome disclosed by the patent contains an arachidonic acid metabolite, two or more lipid-containing bilayers and two or more aqueous compartments containing a release-inhibiting citric acid buffer. About 90% of available prostaglandin was associated or partitioned into multilamellar vesicles when a citrate buffer was used to rehydrate dried lipids to form liposomes. The liposomes are about 500 nm in diameter to about 1 micron in diameter. Prostaglandin comprising from about $10^{-12}$ g to about $10^{-3}$ g of the prostaglandin per kg of the animal's body weight is administered per dose of the composition.

SUMMARY

A pharmaceutical agent may be encapsulated in a multilamellar liposome in the absence of a partition enhancing buffer. The pharmaceutical agent is administered in an amount effective to treat the vascular disease. The release of the pharmaceutical agent from the multilamellar liposome may be regulated by proper selection of liposome size, dosage of the pharmaceutical agent, lipid to pharmaceutical agent weight ratio, and rate of infusion of the pharmaceutical agent.

BRIEF DESCRIPTION OF THE DRAWINGS

So that the manner in which the above recited features, advantages and objects of the present invention are attained can be understood in detail, a more particular description of the invention briefly summarized above, may be had by reference to the embodiments thereof which are illustrated in the appended drawings.

It is noted, however, that the appended drawings illustrate only typical embodiments of this invention and are therefore not to be considered limiting of its scope, for the invention may admit to other equally effective embodiments.

FIG. 1 is a graph of the percentage change in Maximum Walking Distance from baseline by visit of an intent-to-treat population;

FIG. 2 is a graph of the percentage change in Maximum Walking Distance from baseline by visit of an efficacy population;

FIG. 3 is a graph of the percentage change in Pain-Free Walking Distance from baseline by visit of an intent-to-treat population;

FIG. 4 is a graph of the percentage change in Pain-Free Walking Distance from baseline by visit of an efficacy population.

DETAILED DESCRIPTION OF A PREFERRED EMBODIMENT

Figure 5:
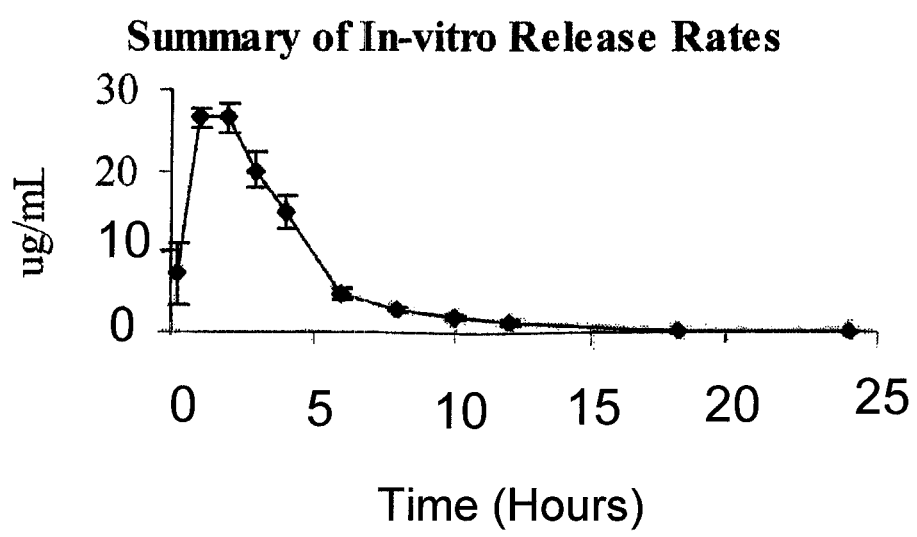
FIG. 5 is a graph representing the in-vitro release rate of liposomal PGE1.

The present invention includes multilamellar liposomes as delivery systems for delivering pharmaceutical agents encapsulated within the multilamellar liposomes into the vascular system of a mammal for treatment of vascular disease.

Liposomes are self-assembling structures comprising one or more bilayers of amphipathic lipid molecules, which form closed spherical structures known as vesicles. The vesicles form when molecules with two hydrocarbon chains, such as phospholipids, are hydrated. Several of these vesicles may typically form one inside the other in diminishing size and thereby form a multilamellar structure of concentric phospholipid spheres separated by layers of fluid. Pharmaceutical agents may be loaded in the liposomes by dissolving the pharmaceutical agents in the medium in which the phospholipids are hydrated. When the liposomes form, hydrophilic pharmaceutical agents may be trapped in the aqueous center of the liposomes. Hydrophobic agents generally associate with the less polar phospholipids in the bilayers. The multilamellar liposomes present numerous barriers through which a pharmaceutical agent, such as PGE1, has to pass in order to leak from the liposome into the external environment. Hydrophobic agents associated with the liposome membranes are released as the liposome bio-layers are dissociated.

Atherosclerosis is a disease of the large arteries that involves accumulation of high molecular weight lipoprotein, called plaque, in the arterial wall. Inflammation in and around the plaque results in the release of cytokines and metalloproteases which attack the endothelium and may lead to leaky arteries. Spaces between endothelial cells may develop where the extracellular matrix is eroded away. The spaces may allow diffusion and extravasation through the arterial wall of molecular substances precluded by normal vessels. In damaged vessels, enhanced absorption of pharmaceutical agents, such as prostaglandin E-1 (PGE1), may occur in a site-directed manner.

PGE1 may be incorporated into multilamellar liposomes composed of egg-derived phosphatidylcholine, with maltose and BHT added to enhance product stability. The multilamellar liposomes may have a diameter in the range of about 200 to 400 nm. More preferably, the liposomes are about 300 nm in diameter. This may be accomplished by passing the liposomal solution, including the pharmaceutical agent entrapped therein, through a homogenizer two or more times at a pressure of about 11,000 psi. After each pass through the homogenizer, a small sample of the liposomal solution is tested to determine the size distribution of the liposomes. When the liposome size distribution is within the preferred range of 200 to 400 nm, the liposomal solution is filtered and lyophilized. During the lyophilizing process, ethanol, BHT and water are removed. The resulting drug composition is a lyophilized liposomal powder stored in 10 cc Type I vials containing 2.0 mg PGE1/250 mg of dehydrated liposomes. The dehydrated liposomes may be stored at minus 20° C. for later use.

Upon rehydration, the lyophilized liposomes are reconstituted with sterile saline. Prior to intravenous administration to a patient, the amount of reconstituted solution for the patient dosage is calculated and added to an intravenous saline infusion bag for administering to the patient.

Liposome Preparation

Approximately 5 L of sterilized water for injection (WFI) may be added to a bottle and cooled to room temperature overnight. The cooled WFI may be sparged with nitrogen for at least 60 minutes. After sparging, 3600 g of the sparged WFI may be added to a 4 L beaker containing 360 g of maltose and mixed for at least 30 minutes until the maltose is dissolved while continuing to sparge with nitrogen. The maltose solution may be filtered through a 0.45 µm Millipak 20 filter at 150±10 rpm into another beaker and sparged with nitrogen after filtration.

In a separate beaker, 17.2 g of egg phosphatidylcholine (EPC) may be combined with 20 g of ethanol and sonicated for at least 20 minutes until the EPC is dissolved.

In a clean TOC sample vial, 0.113 g of butylated hydroxytoluene (BHT) may be combined with 8.2 g of ethanol and sonicated for at least 20 minutes until the BHT is dissolved.

In a separate TOC sample vial, 3.457 g of PGE1 may be combined with 12.168 g of ethanol and sonicated for at least 20 minutes until the PGE1 is dissolved.

The ethanol/EPC solution and the ethanol/BHT solution may be combined in a 100 mL beaker and sonicated for at least 20 minutes until the EPC and BHT are dissolved. The ethanol/PGE1 solution may then be added to the ethanol/EPC/BHT solution and sonicated for at least 20 minutes until all the ingredients are dissolved.

A syringe pump on a scissor jack may be placed over the 4 L beaker containing the Maltose/WFI solution. The Maltose/WFI solution may be mixed at 2500 rpm while maintaining the nitrogen sparge. The ethanol/EPC/BHT/PGE1 solution may be drawn into a 60 cc disposable syringe which is mounted and aligned in the Harvard pump to slowly add 1 mL of the ethanol/EPC/BHT/PGE1 solution to the Maltose/WFI solution in the 4 L beaker. The mixing speed may be slowly increased to 3500 rpm while not allowing the solution to splash or foam during mixing. The disposable syringe may be refilled as necessary until all the ethanol/EPC/BHT/PGE1 solution is added to the Maltose/WFI solution to form a final bulk solution of 3980 g. Mixing of the bulk solution may continue for a minimum of 60 minutes without the nitrogen sparge.

The bulk solution may then be cooled to 20° C. in an ice bath and passed through a homogenizer, for example, an Avestin homogenizer, at 11,000 psi. The first 20 mL of the bulk solution dispensed from the homogenizer may be discarded and the remainder of the bulk solution may be collected in a new, clean 5 L bottle. The temperature of the bulk solution increases as it passes through the homogenizer. The bulk solution may be cooled again to 20° C. and passed through the homogenizer a second time. The process may be repeated a third time. The first 20 mL of the bulk solution dispensed from the homogenizer after the second and third passes is discarded. A total of about 150 mL of the bulk solution is discarded for priming the homogenizer from all three passes of the bulk solution through the homogenizer.

After the third pass through the homogenizer, a 20 mL sample of the bulk solution is tested for liposome size distribution. The target liposome size range is 200 to 400 nm in diameter, with 300 nm in diameter being preferred.

The liposome solution may then be stirred and heated to 65° C. The heated liposome solution may then be filtered through a Sartobran 300 Capsule 0.2 µm filter at 10-20 rpm and collected in a sterile 5 L receiving bottle. Thereafter, 10 cc Type I vials are filled with the liposome solution and lyophilized according to the following process. Each 10 cc Type I vial contains 2.0 mg PGE1/250 mg of dehydrated liposomes.

Lyophilization Process

The 10 cc vials filled with the liposome solution may be loaded in a lyophilizer. The vials are held at −50° C. for about 4 hours at a vacuum of 400 microns. The shelf temperature is then increased to 20° C. and held for about 86 hours at a vacuum of 150 microns. The total lyophilization process is about 90 hours. After the lyophilization process is completed, the lyophilizer vacuum is reduced to 14.7 psi and the vials are stoppered and coded. The lyophilized liposomes may be stored at −20° C. for future use.

In-Vitro Release of Liposomal PGE1

Vials of the lyophilized liposomes were rehydrated and tested to determine the in-vitro release rate of PGE1. Six vials of the lyophilized liposomes were reconstituted with WFI. An in-vitro release study was conducted over a twenty-five hour period using a dissolution system. The graph of FIG. 5 summarizes the PGE1 release rate of the in-vitro release study.

As illustrated in FIG. 5, the PGE1 release profile is characterized by an initial "burst" of PGE1 released during the first hour of the study. Less than 50% of the PGE1 was released during the first hour and PGE1 continued to be released for up to twenty-five hours.

In Vivo Study of Liposomal PGE1

Rehydrated liposomes stored in the 10 cc vials were rehydrated and tested in vivo in a clinical study to determine the effect of liposomal prostaglandin E-1 in patients with critical limb ischemia and intermittent claudication. The study was a Phase II, open label, multicenter study with two screening visits, six treatment visits and two follow-up visits. Each patient had at least a six-month history of critical limb ischemia and intermittent claudication (diagnosis with Rutherford Category 3, 4, or 5 and/or Fontaine Stage II/III). Screening evaluations were performed at visits 1 and 2. At the first visit the screening evaluations included medical history, vital signs, physical exam, ECG, PADWIQ, CLI severity, laboratory assessments, ankle brachial index (ABI), analgesic use, pain score, maximum walking distance (MWD), pain free walking distance (PFWD), quality of life (QOL) assessment, and concomitant medications. At the second visit, vital sings, analgesic use, MWD, PFWD, concomitant medications and adverse events were recorded. Vital signs, ECG, PADWIQ, CLI severity, ABI, analgesic use, pain score, MWD, PFWD, QOL assessment, concomitant medications and adverse events were also recorded at treatment visits 3-8, and all assessments were also performed at the two and four-week follow-up visits after the study was completed.

Ninety-two patients were enrolled in the study. Eighty patients received at least one dose of study medication. Seventy-two patients completed twelve weeks of follow-up. The medication was administered intravenously in six four-hour treatments at the maximum patient tolerated dose in the range of 0.1-2.5 μg/kg/hr once a week.

The primary efficacy endpoint was Maximum Walking Distance (MWD) on a treadmill compared to a baseline mean taken at the two screening visits. The secondary endpoints were rest pain (mean score), percentage of patients with at least a 30% increase in MWD versus baseline (clinically significant response), percentage of patients with at least a 30% increase in PFMWD versus baseline (clinically significant response in Pain Free Maximum Walking Distance), analgesic use, QOL questionnaire, Peripheral Arterial Disease Walking Impairment Questionnaire (PADWIQ), ABI index, pain score and transcutaneous oxygen pressure ($TcPO_2$).

Percentage changes in laboratory assessments from baseline to visit 10 (last visit) were assessed using the paired t-test to determine if any changes in these parameters were statistically significant. Changes in vital signs were assessed in two manners. The first analysis of vital signs evaluated the percentage changes from the screening visit to the last measurements at each follow-up visit, using the paired t-test. This analysis was used to detect statistically significant changes in vital signs over the course of the study. The second analysis of vital signs evaluated the percentage change from pre-dose levels to post-dose time-points within each treatment administration visit to assess the short-term effects of the study medication on vital signs. The paired t-test was used to determine statistically significant changes.

Efficacy was evaluated on two analysis populations, the intent-to-treat population (80 patients receiving at least one dose of study medication) and the efficacy population (patients receiving at least 3 doses of the study medication). The intent-to-treat population consisted of the 80 patients receiving at least one dose of study medication. For the analysis of MWD and PFMWD, patients who failed to perform the treadmill test due to leg pain or resting pain were included in the intent-to-treat analysis. For these patients, the MWD and PFMWD were considered to be zero. Patients that discontinued the study were also included in the intent-to-treat population. For the intent-to-treat analysis, a last-observation-carried-forward approach was utilized to ensure the maximum sample size at each follow-up assessment. The primary efficacy analysis was per protocol analysis of MWD from the baseline at the last treatment visit, and the 2 and 4-week post-treatment visits. The paired t-test was used to determine statistically significant changes from baseline.

Secondary efficacy analysis included the calculation of the proportion of patients with a statistically significant response (at least a 30% increase in MWD and PFMWD). A Z test was used to test for a statistically significant proportion. Additional secondary efficacy analysis included analysis of PFMWD, PADWIQ, ABI, analgesic use, pain score and QOL assessment using the MOS SF-36. These assessments were performed at baseline, the last treatment visit, and at 2 and 4 weeks after the last treatment visit. Changes from baseline were calculated and the paired t-test was used to determine statistically significant changes from baseline.

All tests were declared statistically significant if the calculated p-value was less than or equal to 0.05. All tests appear as two-sided p-values.

As assessed by the primary endpoint of MWD, liposomal prostaglandin E-1 was shown to have a statistically significant benefit in the primary endpoint after treatment in patients with critical limb ischemia and intermittent claudication. Mean percentage improvements from baseline in MWD of 80%, 102%, and 128% were observed at visits 8, 9 and 10 in the intent-to-treat population as illustrated in FIG. 1. These changes were highly statistically significant and results were similar for the efficacy population illustrated in FIG. 2. Results for MWD are presented in Table 1 below:

TABLE 1

SUMMARY OF MAXIMUM WALKING DISTANCE

| Visit | Mean ± SD | % Change from Baseline (P-Value)* |
|---|---|---|
| Intent-to-Treat Population (n = 80) | | |
| Baseline (n = 80) | 240.7 ± 211.5 | — |
| Visit 8 (n = 77) | 385.6 ± 402.00 | 80.1 ± 152.7 (p < 0.0001) |
| Visit 9 (n = 73) | 412.1 ± 448.2 | 101.8 ± 191.9 (p < 0.0001) |
| Visit 10 (n = 73) | 465.0 ± 493.2 | 128.1 ± 226.2 (p < 0.0001) |
| LOCF (n = 80) | 452.1 ± 475.4 | 119.3 ± 218.0 (p < 0.0001) |
| Efficacy Population (n = 75) | | |
| Baseline (n = 75) | 241.5 ± 216.2 | — |
| Visit 8 (n = 71) | 396.5 ± 402.3 | 84.6 ± 152.2 (p < 0.0001) |
| Visit 9 (n = 71) | 420.2 ± 451.4 | 105.4 ± 193.2 (p < 0.0001) |
| Visit 10 (n = 71) | 474.5 ± 496.4 | 132.4 ± 227.7 (p < 0.0001) |

*Paired t-test P-value

Similar results were observed in the secondary endpoint of PFMWD where mean percentage improvements from baseline of 127%, 165%, and 220% were observed at visits 8, 9, and 10, respectively in the intent-to-treat population. Similar results occurred in the efficacy populations. See FIGS. 3 and 4.

Clinical response was defined as a 30% or greater improvement in MWD from baseline. An analysis of the proportion of responders was performed at visits 8, 9, and 10 and 95% confidence intervals were obtained. For the intent-to-treat population, the proportion of responders at visits 8, 9, and 10 was 53%, 58%, and 58%, respectively. The proportion of responders in the efficacy population was slightly higher, 55%, 59%, and 59% at visits 8, 9, and 10, respectively. A similar response definition was determined for the PFMWD. In the intent-to-treat population, the proportion of patients with a 30% or greater improvement in PFMWD was 70%, 67%, and 77% at visits 8, 9, and 10, respectively. For the efficacy population, the proportion of PFMWD responders was 72%, 69%, and 79% at visits 8, 9, and 10, respectively.

Percentage increases from baseline in the Ankle-Brachial Index (ABI) for both the right and left side were observed at visits 8, 9, and 10 for both the intent-to-treat and efficacy populations. These percentage increases were statistically significant at visits 8 and 10 for both sides in the intent-to-treat and efficacy populations.

Additionally, the Peripheral Arterial Disease Walking Impairment Questionnaire (PADWIQ) was completed for each patient at the study visits. The PADWIQ assessed Walking Impairment, Walking Distance, and Walking Speed. Slight improvements from baseline were observed in most aspects of the Walking Impairment sections and significant improvement was particularly noted in calf pain, aching, or cramps from baseline (18% vs.>49%, 47%, and 47% of patients with slight or no difficulty with calf pain) at visits 8, 9, and 10. Results were similar in the efficacy population.

Statistically significant improvements from baseline were observed in the Walking Distance section of the PADWIQ. At visits 8, 9, and 10, the percentage increases in the Walking Distance Score from baseline were 128%, 193%, and 186%, respectively in the intent-to-treat population, and 128%, 196%, and 188%, respectively in the efficacy population. Only percentage changes in walking greater than 500 meters did not improve from baseline.

Statistically significant improvements from baseline were also observed in the Walking Speed section of the PADWIQ. At visits 8, 9, and 10, the percentage increases in the Walking Speed Score from baseline were 55%, 74%, and 69%, respectively, in the intent-to-treat population and 55%, 75%, and 70%, respectively, in the efficacy population. Only the percentage change in running/jogging 300 meters did not significantly change from baseline.

The MOS SF 36 was used to assess improvements in the quality of life. Improvements were noted in both the mental and physical components of the SF-36, as well as in all of the subscales at visits 8, 9, and 10. Statistically significant improvements in the Physical Component (9.4%, 8.8%, 10.3%), as well as the Role Physical (29 to 35% improvement), Bodily Pain Index (29% to 32% improvement), General Health (41% to 53% improvement), Social Function (16% to 19% improvement) and Role Emotional (19% to 27% improvement) subscales were observed at visits 8, 9, and 10 in both the intent-to-treat and efficacy populations. At visits 8 and 9, statistically significant improvements were also observed in the Physical Function (21% to 24%) and Vitality (10%) subscales in both analysis populations.

Transcutaneous Oxygen Pressure ($TcPO_2$) measurements were taken at baseline and follow-up visits at one study site. Although the sample size was markedly reduced, statistically significant percentage improvements in $TcPO_2$ of 73%, 71%, and 74% were observed for the $O_2$ measurements and 9%, 10%, and 11% were observed for the elevation measurement at visits 8, 9, and 10, respectively. Results were similar for both the intent-to-treat and efficacy populations.

No significant changes from baseline were observed in two secondary efficacy endpoints of analgesic use and rest pain. However, slight improvements in the number of analgesics used were observed. Non-significant increases from baseline in rest pain were noted. The median percentage change in rest pain from baseline was 0%.

The results of this study indicate that treatment with liposomal prostaglandin E-1 is effective for treatment of critical limb ischemia and intermittent claudication as a result of peripheral arterial disease. Statistically significant improvements from baseline were observed for the primary efficacy endpoint of Maximum Walking Distance, as well as for most of the disease related secondary efficacy endpoints (seven of the nine secondary endpoints showed significant improvement from the baseline). In this study significant improvement in responses was observed four (4) weeks post-treatment, compared with one (1) to two (2) weeks for treatment with standard prostaglandin. The results of the study suggest that liposomal prostaglandin E-1 provides improvements in the symptoms and quality of life of patients with critical limb ischemia and intermittent claudication.

Medication Dosage

The drug dosage per treatment visit was calculated based on the maximum dose tolerated by each patient. At the first treatment visit (visit 3), each patient was administered an initial dose of 0.5 μg/kg/hr, where the weight of the patient is measured in kilograms (kg). The dose was escalated within each patient until the tolerance or maximum dose was achieved. The maximum dose from this first treatment visit was then administered at the subsequent treatment visits (visit 4 through 8). The amount of reconstituted liposomal PGE1 solution added to the infusion saline solution was determined for each patient as hereinafter described.

Assuming 2.0 mg PGE1 per vial reconstituted in 5 mL of saline (or 400 μg/mL), a 75 kg patient scheduled to be dosed at 1.5 μg/kg/hr would be infused with a total dose of 450 μg of PGE1 in 200 mL of infusion solution over 4 hours at an infusion rate of 50 mL per hour. The amount of reconstituted liposomal PGE1 solution to be added to a 500 mL IV bag of 0.9% saline solution to the total infused dosage of PGE1 for the 75 kg patient is calculated by the formula: 450 μg/400 μg/mL×500 mL/200 mL=2.8 mL. Using sterile 10 ml tuberculin syringes, 2.8 mL of saline is removed from the 500 mL IV bag and 2.8 mL of reconstituted liposomal PGE1 solution is added to the 500 mL IV bag and the patient is infused at 50 mL per hour for four hours.

The preceding description has been presented with references to presently preferred embodiments of the invention. Those skilled in the art and technology in which this invention pertains will appreciate that alteration and changes in the described structure may be practiced without meaningfully departing from the principal, spirit and scope of the invention. Accordingly, the foregoing description should not be read as pertain only to the precise methods described but rather should be read consistent with and as support by the following claims which are to have the fullest and fair scope.

The invention claimed is:

1. A method of treating vascular disease in a mammal, the method comprising administering a liposomal composition comprising a pharmaceutical agent encapsulated in liposomes in an amount effective to improve the symptoms of the vascular disease, said liposomes being characterized by the absence of a partition-enhancing buffer, and wherein an effective amount of said pharmaceutical agent comprises administering from about 0.1 to 2.5 μg of said pharmaceutical agent per kg of the mammal's body weight per hour in four-hour treatments once per week.

2. The method of claim 1 wherein said pharmaceutical agent is a prostaglandin.

3. The method of claim 1 wherein said pharmaceutical agent is prostaglandin E-1.

4. The method of claim 1 wherein said liposomes are multilamellar.

5. The method of claim 4 wherein said liposomes have a size distribution range of about 200 nm to 400 nm in diameter.

6. The method of claim 5 wherein said liposomes have a diameter of about 300 nm.

7. The method of claim 1 including lyophilizing and storing said liposomes prior to use, and further including rehydrating said liposomes with water for injection (WFI) prior to administering said liposomal composition.

8. The method of claim 1 wherein said pharmaceutical agent is released from said liposomes into the mammal's vascular system for up to twenty-five hours after said administering step.

9. The method of claim 8 wherein less than 50% of said pharmaceutical agent is released from said liposomes into the mammal's vascular system within one hour after said administering step.

10. The method of claim 1 wherein said administering step includes adding said liposomal composition to an infusion solution and intravenously administering said infusion solution at a rate of 50 mL per hour for four hours.

11. The method of claim 1 wherein said mammal is a human.

12. The method of claim 1 wherein said vascular disease is peripheral vascular disease.

13. The method of claim 1 wherein said vascular disease is critical limb ischemia.

14. The method of claim 1 wherein said vascular disease is intermittent claudication.

15. The method of claim 10 wherein said administering step includes administering said liposomal composition once a week for at least six weeks.

\* \* \* \* \*